United States Patent [19]

Buckley et al.

[11] 3,950,349

[45] Apr. 13, 1976

[54] N-(N-1′,2′-BENZISOTHIAZOLIN-3′-3′-ONYLCARBONYLTHIO)-1,2-BENZISOTHIAZOLIN-3-ONE

[75] Inventors: Alan John Buckley; Edward George Gazzard; Michael Singer; John Anthony Taylor, all of Manchester, England

[73] Assignee: Imperial Chemical Industries Limited, London, England

[22] Filed: Apr. 4, 1974

[21] Appl. No.: 458,040

[30] Foreign Application Priority Data

Apr. 19, 1973  United Kingdom............... 18959/73

[52] U.S. Cl. .............................. 260/304 A; 424/270
[51] Int. Cl.$^2$ ..................................... C07D 277/74
[58] Field of Search.......................... 260/304, 304 A

[56] References Cited
UNITED STATES PATENTS 3,761,489   9/1973   Grivas................................. 260/304

OTHER PUBLICATIONS

Ponci et al., *Chem. Abstracts*, 66: 37816j (1967).

*Primary Examiner*—Richard J. Gallagher
*Assistant Examiner*—D. B. Springer
*Attorney, Agent, or Firm*—Cushman, Darby & Cushman

[57]  ABSTRACT

The invention provides certain N-thio substituted isothiazolin-3-one compounds and process for their manufacture, and includes their use in protecting media which are susceptible to infection by micro-organisms against such infection and the suppression of infection in media already infected. These compounds provide a quicker kill of micro-organisms than the parent isothiazolin-3-ones.

1 Claim, No Drawings

N-(N'-1',2'-BENZISOTHIAZOLIN-3'-ONYLCARBONYLTHIO)-1,2-BENZISOTHIAZOLIN-3-ONE

This invention relates to biocides and more particularly to biocidal compounds which are isothiazolin-3-one derivatives.

1,2-Benzisothiazolin-3-one, its nuclear-substituted halogen derivatives and certain other isothiazolin-3-one derivatives are known to be effective agents against bacteria, fungi, algae and other organisms and are particularly useful for the protection of aqueous media against infection by microorganisms.

Although effective, these known compounds are largely bacteriostatic and fungistatic and tend to be somewhat slow-acting.

It has now been found that certain N-thio-substituted derivatives of isothiazolin-3-ones are effective biocides which in general are faster acting than the previously known derivatives.

According to the present invention there are provided N-thio-substituted isothiazolin-3-one compounds having the general formulae

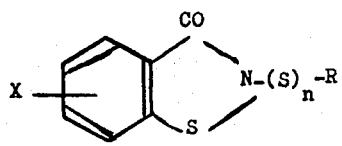

or

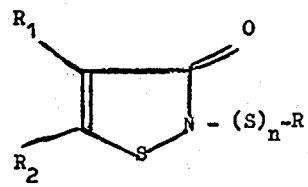

wherein X represents a hydrogen atom, a halogen atom, a $C_1$–$C_4$ alkyl or alkoxy group, a nitro group or a cyano group.

$R_1$ represents a hydrogen atom, a halogen atom, a $C_1$ – $C_4$ alkyl group or a cyano group.

$R_2$ represents a $C_1$ – $C_4$ alkylsulphinyl or alkylsulphonyl group or an aralkyl sulphinyl or aralkylsulphonyl group having up to 8 carbon atoms when $R_1$ is cyano.

$R_2$ represents a hydrogen atom, a halogen atom, an aralkyl group having up to 8 carbon atoms or a $C_1$ – $C_4$ halogeno-alkyl group when $R_1$ is a $C_1$ – $C_4$ alkyl group or a halogen atom, provided that $R_2$ can be a $C_1$ – $C_4$ alkyl group when $R_1$ is a $C_1$ – $C_4$ alkyl group, and $R_2$ represents an aralkyl group having up to 8 carbon atoms or a $C_1$ – $C_4$ halogeno alkyl group when $R_1$ is hydrogen.

R represents a $C_1$ – $C_{12}$ alkyl group, a $C_2$ – $C_{12}$ substituted alkyl group, an aryl group which may be substituted by one or more atoms or groups selected from halogen, $C_1$ – $C_4$ alkyl, aminocarbonyl, mono- and di-($C_1$–$C_4$) alkylaminocarbonyl, carboxyl, alkoxy ($C_1$–$C_4$) carbonyl, an aralkyl group, a group of the formula

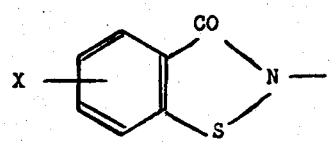

or

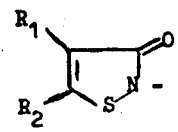

wherein X, $R_1$ and $R_2$ have the meanings defined above, or a group of the formula:

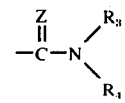

wherein Z is oxygen or sulphur and $R_3$ and $R_4$ each independently represent a $C_1$ – $C_4$ alkyl group or $R_3$ and $R_4$ together with the N atom form a group of the formula:

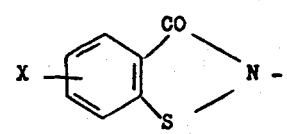

or

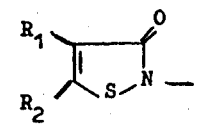

wherein X, $R_1$ and $R_2$ have the meanings defined above, and $n$ is 1 or 2; and isothiazolin-3-one compounds having the general formulae:

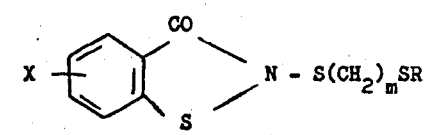

or

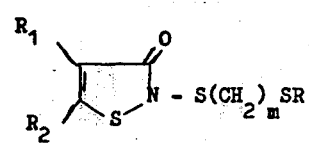

wherein X, $R_1$ and $R_2$ have the meanings defined above, R represents a hydrogen atom or the meanings defined above and $m$ is an integer from 2 to 6.

Preferred compounds are 1,2-benzisothiazolin-3-ones in which the substituent X is a hydrogen atom.

It is preferred that when R represents a substituted aryl group, the said group is a phenyl group having a substituent ortho to the point of attachment of the phenyl group to the sulphur atom. It is further preferred that the substituent is an o-aminocarbonyl group or an o-ethoxycarbonyl group and that the phenyl nucleus is additionally substituted by a chlorine or a bromine atom or by a methyl group.

The compounds according to the present invention are in general prepared by the reaction of a salt of an isothiazolin-3-one having the formula

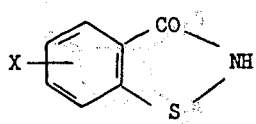

or

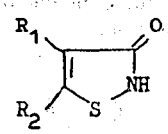

wherein X, $R_1$ and $R_2$ have the meanings defined above, with the corresponding sulphenyl halide under substantially anhydrous conditions in an inert solvent. The salt is preferably an alkali metal salt, especially the sodium salt. The isothiazolin-3-one starting materials are known compounds.

Alternatively compounds of this invention can be prepared by reaction of the free isothiazolin-3-one with the corresponding sulphenyl halide, in presence of an acid binding agent such as triethylamine, under substantially anhydrous conditions, in an inert solvent.

The invention also provides a method for the protection of media which are susceptible to infection by micro-organisms against infection thereby and for the suppression of such infection in media already infected, which comprises incorporating into the media from 1 to 10000 parts per million by weight of an N-thio-substituted isothiazolin-3-one compound as hereinbefore defined. The N-thio-substituted isothiazolin-3-one compounds provide a quicker kill against micro-organisms than the parent isothiazolin-3-ones.

The compounds according to the invention are useful, for example, as slimicides in the water systems of paper mills, in the preservatives of leather, adhesives and wood against attack by bacteria and fungi, for the in-can preservation of water-based paints and protection of paint films against fungal attack, for the protection of aqueous oil emulsions, such as the cutting oils used as lubricants and coolants in the machining of metal, against bacterial infection and in aqueous media generally to prevent or remove infection by bacteria, fungi and algae and for the preservation of skins and hides.

The invention is illustrated but not limited by the following Examples in which parts and percentages are by weight.

EXAMPLE 1

Preparation of N-Isopropylthio-1,2-benzisothiazolin-3-one 15.1 parts of 1,2-benzisothiazolin-3-one are dissolved in 218 parts of toluene and 12.8 parts of a 32% aqueous sodium hydroxide solution are added dropwise to the solution. The mixture is heated with stirring and water is distilled off as the toluene azeotrope.

Meanwhile, 13.5 parts of sulphuryl chloride are added dropwise to 7.5 parts of isopropyl mercaptan stirred at a temperature below 10°C. Nitrogen is blown through the solution to remove hydrogen chloride and sulphur dioxide. The sulphenyl chloride so produced is then added dropwise to the stirred suspension of 1,2-benzisothiazolin-3-one sodium salt. An exothermic reaction causes the temperature to rise to 40°C. The resulting suspension is filtered and the filtrate is evaporated to dryness under reduced pressure. The residual white solid is recrystallized from a chloroform/petroleum ether mixture to give 8.7 parts of product having m.p. 91° – 92°C. Elementary analysis and infra red and nuclear magnetic resonance spectra confirm the structure of the product.

EXAMPLE 2

Comparison between the effectiveness of 1,2-benzisothiazolin-3-one (I) and its N-isopropylthio derivative (II) in the control of microbial growth in an aqueous oil emulsion.

The compounds are compared by adding increasing quantities by weight to 2000 parts by volume of the infected emulsion, as set out in the table below (i.e. a solution defined as containing 10 ppm contains 20 mg per 2000 ml of solvent):

Numbers of Surviving Bacteria (cells/ml) in Emulsion
(determined in nutrient agar)

| Compound | 8 days after A | 3 days after B | 3 days after C | 7 days after D | 3 days after E |
|---|---|---|---|---|---|
| I (A) | $12 \times 10^5$ (B) | $110 \times 10^5$ (C) | $65 \times 10^5$ (D) | $184 \times 10^5$ (E) | $200 \times 10^5$ |
| II (A) | $3.6 \times 10^5$ (B) | $12 \times 10^5$ (C) | $8.9 \times 10^5$ (D) | $4.3 \times 10^5$ (E) | $<10$ |
| Control | $7.7 \times 10^5$ | $32 \times 10^5$ | $2.9 \times 10^5$ | $9.7 \times 10^5$ | $16 \times 10^5$ |

(A) 10 ppm of test chemical added
(B) 20 " (i.e. total 30 ppm)
(C) 20 " ( " 50 ")
(D) 50 " ( " 100 ")
(E) 100 " ( " 200 ")

The results indicate that at concentrations of 10 to 50 ppm the two compounds show no marked difference in activity. Three days after 100 ppm of the compound had been added in each case, the N-isopropylthio derivative (II) had markedly reduced the bacterial count in contrast to the parent compound I (i.e. total addition of each compound 200 ppm).

EXAMPLE 3

Comparison of the effectiveness of 1,2-benzisothiazolin-3-one (I) and its N-isopropylthio derivative (II) in the control of microbial growth in an emulsion paint.

The test compounds are added to 200 parts of naturally-infected paint to provide concentrations of 50, 75 and 100 ppm (weight for weight) of the active ingredients. The numbers of surviving bacteria are determined at intervals as shown below, and the surviving bacterial cells are further enumerated after the paints had each received an artificial inoculation of contaminated paint on the 13th day of the test.

| Treatment and concentration (ppm active ingredient) | Survivors in paint (cells/g. on nutrient agar) after | | | | |
|---|---|---|---|---|---|
| | 0 days | 3 days | 7 days | 13 days* | 18 days |
| I 100 | No count | $5.4 \times 10^3$ | <10 | No count | <10 |
| 75 | " | $2.4 \times 10^4$ | $8.5 \times 10^4$ | $2.75 \times 10^4$ | $4.8 \times 10^4$ |
| 50 | " | $2.2 \times 10^4$ | $11.9 \times 10^4$ | $36 \times 10^4$ | $10.9 \times 10^5$ |
| II 100 | " | <10 | <10 | <10 | <10 |
| 75 | " | <10 | <10 | $1.7 \times 10^2$ | <10 |
| 50 | " | <10 | <10 | $1.5 \times 10^3$ | <10 |
| Control | $6.2 \times 10^6$ | $5.6 \times 10^6$ | $1.6 \times 10^5$ | $10.5 \times 10^6$ | $3.9 \times 10^5$ |

*After paint samples had been taken on thirteenth day, 1 ml. of heavily contaminated paint was added to each variant.

These results indicate that under the experimental conditions the N-isopropylthio derivative (II) was more active than the parent compound (I) by a factor of two and has a more rapid biocidal effect.

EXAMPLE 4

Comparison of the bactericidal activity of 1,2-benzisothiazolin-3-one (I) and its N-isopropylthio derivative (II) during a short incubation period in emulsion paint.

I and II were prepared as 1% solution in dimethylformamide, the solutions then being added to samples of infected emulsion paint to provide concentrations of 50, 75 and 100 ppm. Surviving bacteria were determined and the results are shown below. The control which contained no biocide received an addition of dimethylformamide in amount equal to that added with 100 ppm of biocide.

spectrum which indicated a ratio of aliphatic to aromatic protons of 2:9, consistent with the formula:

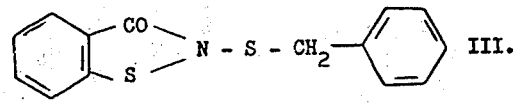

EXAMPLE 6

Preparation of N-phenylthio-1,2-benzisothiazolin-3-one (IV)

8.94 parts of sulphuryl chloride in 30 parts of carbon tetrachloride were added at 10°C to 7.28 parts of thiophenol dissolved in 30 parts of carbon tetrachloride and the solution was degassed with nitrogen.

The solution was then added to a suspension of 11.4 parts of the sodium salt of 1,2-benzisothiazolin-3-one in

| Treatment | Surviving bacteria/g. after | | | | | | |
|---|---|---|---|---|---|---|---|
| | 0 | 4 hr. | 8 hr. | 24 hr. | 30 hr. | 50 hr. | 75 hr. |
| I 100 ppm | — | $6.9 \times 10^4$ | $8.4 \times 10^4$ | $5 \times 10^2$ | $3 \times 10^2$ | <10 | <10 |
| 75 ppm | — | $8.7 \times 10^4$ | $2 \times 10^4$ | $6 \times 10^3$ | $6 \times 10^2$ | $2 \times 10^2$ | <10 |
| 50 ppm | — | $1.07 \times 10^5$ | $4 \times 10^5$ | — | — | $1 \times 10^3$ | $3 \times 10^2$ |
| II 100 ppm | — | $2.6 \times 10^4$ | $1.2 \times 10^4$ | <10 | <10 | <10 | <10 |
| 75 ppm | — | $3.1 \times 10^4$ | $1.8 \times 10^4$ | <10 | <10 | <10 | <10 |
| 50 ppm | — | $7.3 \times 10^4$ | $.2 \times 10^4$ | $8 \times 10^2$ | $1.3 \times 10^2$ | <10 | <10 |
| Control | $8 \times 10^5$ | $8.9 \times 10^5$ | $2 \times 10^6$ | $1.1 \times 10^6$ | $1.9 \times 10^6$ | $2.4 \times 10^6$ | $8 \times 10^6$ |

— indicates no count made.

It is clear from the above that the N-isopropylthio derivatives (II) has a markedly more rapid bactericidal action than the parent compound (I).

EXAMPLE 5

Preparation of N-benzylthio-1,2-benzisothiazolin-3-one (III)

8.94 parts of sulphuryl chloride dissolved in 30 parts of carbon tetrachloride were added at 10°C to 8.22 parts of benzylmercaptan in 30 parts of carbon tetrachloride and the solution was degassed with nitrogen. The clear solution was added to a suspension of 11.4 parts of the sodium salt of 1,2-benzisothiazolin-3-one in 140 parts of dry toluene. The resulting suspension was stirred for 18 hours at room temperature and then filtered. The toluene was removed from the filtrate to yield 16.9 parts of a yellow solid which was recrystallised from methanol. The product III had m.p.

111°–112°C and the structure was confirmed by elementary analysis and by determination of the N.M.R.

140 parts of dry toluene, the mixture was stirred at room temperature for 18 hours, and filtered. The toluene was removed from the filtrate to yield 14.5 parts of a red oil which consists of a mixture of diphenyl disulphide with the desired product. Washing of the oil with cold toluene, and recrystallisation of the residue from ethanol gave 7 parts of (IV) having a m.p. 122°C. The structure

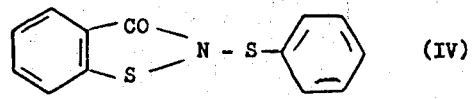

was confirmed by elementary analysis.

EXAMPLE 7

Preparation of N-(N'-1',2'-benzisothiazolin-3'-onylcarbonylthio)-1,2-benzisothiazolin-3-one (V)

1.85 parts of chlorocarbonylsulphenyl chloride in 10 parts of toluene were added to 5.2 parts of the sodium salt of 1,2-benzisothiazolin-3-one suspended in 70 parts of toluene. The resulting suspension was stirred at room temperature for 18 hours and filtered. The toluene was removed from the filtrate to yield 4.1 parts of a yellow solid which was recrystallised from ethanol to give 3.5 parts of (V), m.p. 94°–95°C. The structure

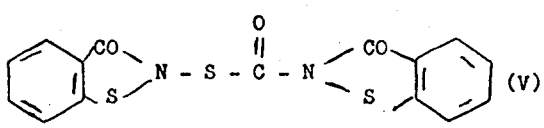

was confirmed by elementary analysis and by the presence in the infra-red spectrum of three carbonyl bands.

EXAMPLE 8

Preparation of N-2'-methoxycarbonylphenylthio-1,2-benzisothiazolin-3-one (VI)

A solution of 7 parts of bromine in 16 parts of carbon tetrachloride was added, with stirring, to 6.72 parts of methyl-o-mercaptobenzoate dissolved in 16 parts of carbon tetrachloride. The clear red solution thus obtained was added to 6.92 parts of the sodium salt of 1,2-benzisothiazolin-3-one suspended in 44 parts of dry benzene. The resulting suspension was stirred at room temperature for 50 hours and was then filtered. The filter cake was well drained, washed with water and dried. This material is a mixture of the required product together with bis(2-methoxycarbonyl phenyl)disulphide, and was recrystallised once from a dimethylformamide-water mixture and once from dioxan to give 1.2 parts of a crystalline solid (VI) having m.p. 185°–187°C. The structure of the compound

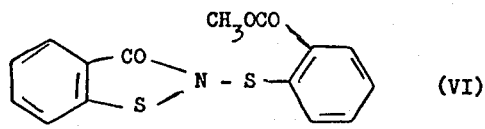

is supported by the infra-red spectrum showing bands at 1680 cm$^{-1}$ and 1280–1320 cm$^{-1}$ with the absence of disulphide absorption and also by the NMR spectrum which showed only one methyl group for every eight aromatic protons.

EXAMPLE 9

Preparation of N-(6'-mercaptohexamethylene-1'-thio)-1,2-benzisothiozalin-3-one (VII)

2.68 parts of sulphuryl chloride in 16 parts of carbon tetrachloride were added at 10°C to 2.5 parts of 1,6-dimercaptohexane in 16 parts of carbon tetrachloride and the solution was degassed with nitrogen.

The clear solution was added to a suspension of 5.7 parts of the sodium salt of 1,2-benzisothiazolin-3-one in 70 parts of dry toluene. The resulting suspension was stirred at room temperature for 18 hours and filtered. The toluene was removed from the filtrate to yield a yellow oil, which was extracted with 80 parts of ethanol. Reduction of the ethanol extract to dryness gave 4.2 parts of a yellow solid, which was recrystallised from ethanol to give 3.5 parts of (VII), m.p. 125°–127°C. The structure

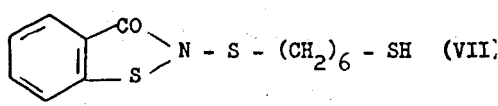

was confirmed by elementary analysis and by the NMR spectrum which indicated a ratio of aromatic to aliphatic protons of 1:3.

EXAMPLE 10

The following compounds were tested for bacteriostatic and fungistatic activity:

(the Roman numerals correspond with those identifying these compounds in Examples 2 and 5–8)

II. N-isopropylthio-1,2-benzisothiozolin-3-one.
III. N-benzylthio-1,2-benzisothiazolin-3-one.
IV. N-phenylthio-1,2-benzisothiazolin-3-one.
V. N-(N'-1',2'-benzisothiazolin-3'-onylcarbonylthio)-1,2-benzisothiazolin-3-one
VI. N-2'-methoxycarbonylphenylthio-1,2-benzisothiazolin-3-one.

The test compounds were added to nutrient agar or malt agar to provide a concentration of 100 ppm, and the media were poured into Petri dishes. After solidification of the agar media, surface (streak) inoculations were made with the bacteria *Pseudomonas aeruginosa*, *Escherichia coli* and *Staphylococcus aureus* on to nutrient agar and central spot inoculations were made with the fungi *Aspergillus niger*, *Pullularia pullulans*, *Chaetomium globosum*, *Alternnaria tenuis*, *Polystictus versicolor* and *Trichoderma viride* on to malt agar. The nutrient agar plates were incubated for 24 hours at 37°C and the malt agar plates for 5 days at 25°C, after which the inoculated Petri dishes were examined for the presence or absence of growth.

The above five compounds totally inhibited the growth of all the test organisms at 100 ppm.

EXAMPLE 11

The compound N-(6'-mercaptohexamethylene-1'-thio)-1,2-benzisothiazolin-3-one (VII) was tested for bacteriostatic and fungistatic activity by the same method and against the same organisms as described in Example 10. At a concentration of 100 ppm the compound totally inhibited the growth of the bacteria *S. aureus* and *E. coli* and the fungi *Alt.tenuis, Chaetomium globosum* and *Polystictus versicolor*.

EXAMPLE 12

Comparison of the bactericidal activity of 1,2-benzisothiazolin-3-one (I) and the N-thiosubstituted derivatives II, III and V.

A suspension in water was made of an overnight nutrient agar culture of the bacterium *Escherichia coli* (strain 5934) and one ml of this suspension was added to a 100 ml aliquot of water containing the test compound at the desired concentration. Samples were removed after various contact times in order to determine the surviving bacterial cell count.

Results are given in the following table.

| Compound and Concentration | SURVIVING BACTERIA (cells/ml) AFTER CONTACT PERIODS OF: | | | |
|---|---|---|---|---|
| | 6 hours | 17 hours | 24 hours | 41 hours |
| None (control) | $3.5 \times 10^7$ | $1.3 \times 10^7$ | $2.4 \times 10^7$ | $2.1 \times 10^7$ |
| I, 100 ppm | — | $1.5 \times 10^7$ | $1.0 \times 10^7$ | $>3 \times 10^5$ |
| 500 ppm | $1.3 \times 10^7$ | — | $<10$ | — |
| II, 100 ppm | — | $5.5 \times 10^6$ | $6.2 \times 10^3$ | $<10$ |
| 500 ppm | $<10$ | — | $<10$ | — |
| III, 100 ppm | — | $1.3 \times 10^7$ | $1.2 \times 10^7$ | $8.6 \times 10^4$ |
| 500 ppm | $1.9 \times 10^7$ | — | $<10$ | — |
| V, 100 ppm | — | $<10$ | $<10$ | $<10$ |
| 500 ppm | $<10$ | — | $<10$ | — |

These results indicate that II, III and V all have a more rapid bactericidal effect on *E. coli* than I over the time period of the experiment.

EXAMPLE 13

Comparison of the fungicidal activities of I and the N-thiosubstituted derivatives II, III and V.

Sterilised 1 cm square nylon meshes on malt agar are seeded with a spore suspension of *Aspergillus niger* and incubated for 24 hours at 25°C, after which period the meshes are covered with fungal mycelium while no spore formation has commenced.

The test chemicals are prepared at the required concentration in 100 ml volumes of water in 250 ml conical flasks. Four fungus-seeded squares are transferred into each flask, which is then rotated on an orbital shaker. Two meshes are removed after 3 hours and the remaining two meshes after 6 hours of incubation, in each case. Each mesh is vigorously shaken in 15 ml of sterile water before being transferred on to a malt agar plate. The latter is then incubated for 3 days at 25°C, after which the nylon meshes are examined for the presence or absence of fungal growth. A complete kill of the fungal mycelium is indicated by the absence of any growth on or around the nylon mesh on the malt agar plate.

Results are given in the following table:

| Compound and Concentration | Survival of fungal mycelium after: | |
|---|---|---|
| | 3 hours | 6 hours |
| None (control) | + | + |
| I, 100 ppm | + | + |
| 250 ppm | + | + |
| II, 100 ppm | + | + |
| 250 ppm | + | — |
| III, 100 ppm | + | + |
| 250 ppm | + | — |
| V, 100 ppm | + | + |
| 250 ppm | + | — |

In this table
+ indicates fungal growth, i.e. no kill
— indicates no fungal growth, i.e. total kill.

These results demonstrate that the N-thiosubstituted derivatives II, III and V, but not I, totally kill the fungal mycelium over a period of six hours.

EXAMPLE 14

Comparison of the bactericidal activities of I and the N-thiosubstituted derivatives II, III, IV and V in an aqueous oil emulsion.

1 litre of an aqueous oil emulsion containing 5% of Presol 44(Mobil) oil was prepared and infected with a small volume of a naturally infected emulsion. After incubation at 30°C for 4 days the 1 litre batch of emulsion was highly contaminated with bacteria. 100 ml samples were removed from the batch and transferred to separate bottles. To each sample was added one of the test biocides to provide a concentration of 200 ppm. The samples were then incubated at 30°C and aliquots were removed after 1 day and 3 days to determine the numbers of surviving bacteria.

Results are given in the following table:

| Compound | Survivors (cells/ml) after incubation period of | |
|---|---|---|
| | 1 day | 3 days |
| None (control) | $9.9 \times 10^6$ | $>3 \times 10^7$ |
| I | $3.5 \times 10^3$ | $3.7 \times 10^4$ |
| II | $6.1 \times 10^3$ | $<10$ |
| III | $8.8 \times 10^3$ | $6.4 \times 10^2$ |
| IV | $9.2 \times 10^3$ | 100 |
| V | 20 | 80 |

It is apparent from these results that the four N-thiosubstituted derivatives II, III, IV and V reduced the bacterial count in the oil emulsion more rapidly than I over the 3-day incubation period of the test.

EXAMPLE 15

Comparison of the activities of I and the N-thio substituted derivative II in the reduction of the bacterial count in the white water of a paper mill.

A white water medium comprising starch 0.3 part, clay 0.3 part, titanium dioxide 0.2 part, animal glue 0.01 part, wet strength resin 0.3 part, sodium aluminate 0.2 part, alum as required to give pH 5, rosin 0.2 part, peptone 10 parts, glucose 25 parts, ground wood 100 parts and tap water 10000 parts, was innoculated with a mixture of nine bacterial cultures which had been isolated from a paper mill backwater.

The contaminated medium is transferred in 100 ml volumes to 250 ml flasks, the biocide is added at the appropriate concentration and the flasks are incubated at 25°C in an orbital shaker. The zero time count is determined and samples are removed from the flasks after 24, 48 and 72 hours in order to determine the numbers of surviving bacteria.

Results are given in the following table:

| Compound and Concentration | Surviving bacteria (cells/ml) after contact times of | | |
|---|---|---|---|
| | 24 hours | 48 hours | 72 hours |
| None (control) | $>3 \times 10^7$ | $>3 \times 10^7$ | $>3 \times 10^7$ |
| I. 50 ppm | $3.1 \times 10^5$ | $2.2 \times 10^2$ | 70 |
| 25 ppm | $6.6 \times 10^3$ | $1.2 \times 10^4$ | $5.4 \times 10^5$ |
| II. 50 ppm | 47 | <10 | <10 |
| 25 ppm | $1.2 \times 10^5$ | <10 | <10 |

It is clear from these results that the N-thiosubstituted derivative II is much more effective than I in reducing the bacterial count in white water medium.

We claim:

1. The compound N-(N'-1',2'-benzisothiazolin-3'-onylcarbonylthio)-1,2-benzisothiazolin-3-one.

\* \* \* \* \*